United States Patent
Sakane et al.

(10) Patent No.: US 8,162,855 B2
(45) Date of Patent: Apr. 24, 2012

(54) MEDICAL GUIDE WIRE AND PROCESS FOR PRODUCTION THEREOF

(75) Inventors: Shinichi Sakane, Otsu (JP); Hiroshi Yamada, Otsu (JP); Jun Kogamori, Otsu (JP); Chisaka Aoyama, Otsu (JP)

(73) Assignee: Seven Dreamers Laboratories, Inc., Redwood Shores, CA (US)

( * ) Notice: Subject to any disclaimer, the term of this patent is extended or adjusted under 35 U.S.C. 154(b) by 1326 days.

(21) Appl. No.: 10/527,417

(22) PCT Filed: Sep. 17, 2003

(86) PCT No.: PCT/JP03/11807
§ 371 (c)(1),
(2), (4) Date: Mar. 11, 2005

(87) PCT Pub. No.: WO2004/026385
PCT Pub. Date: Apr. 1, 2004

(65) Prior Publication Data
US 2006/0073264 A1  Apr. 6, 2006

(30) Foreign Application Priority Data
Sep. 20, 2002  (JP) .................................. 2002-276139

(51) Int. Cl.
*A61M 25/00* (2006.01)
(52) U.S. Cl. ...................................................... 600/585
(58) Field of Classification Search .................. 600/585, 600/433, 434; 428/402, 403, 407; 604/164.13; 427/2.1, 2.23
See application file for complete search history.

(56) References Cited

U.S. PATENT DOCUMENTS

| | | | |
|---|---|---|---|
| 4,345,602 A | 8/1982 | Yoshimura et al. | |
| 5,404,887 A * | 4/1995 | Prather | 600/585 |
| 5,626,907 A * | 5/1997 | Hagiwara et al. | 427/202 |
| 5,879,804 A | 3/1999 | Tsubuku | |
| 5,924,998 A | 7/1999 | Cornelius et al. | |
| 6,086,970 A | 7/2000 | Ren | |
| 6,251,085 B1 | 6/2001 | Tezuka | |
| 6,291,054 B1 * | 9/2001 | Thomas et al. | 428/141 |
| 6,390,992 B1 | 5/2002 | Morris et al. | |
| 2002/0082524 A1 * | 6/2002 | Anderson et al. | 600/585 |

(Continued)

FOREIGN PATENT DOCUMENTS
EP  0 407 965 A1  1/1991
(Continued)

OTHER PUBLICATIONS
Plastics International PTFE Data Sheet. Printed Nov. 13, 2009.*

*Primary Examiner* — Max Hindenburg
*Assistant Examiner* — Jonathan M Foreman
(74) *Attorney, Agent, or Firm* — Humre, Schumann, Mueller & Larson, P.C.

(57) ABSTRACT

A medical guide wire (1) is made in which at least a fluororesin coating layer (13) is formed on the surface of a metal wire (11), wherein particulate matter is present in the fluororesin coating layer (13), and the fluororesin coating layer covers the particulate matter and at least some of the particulate matter is formed in surface protrusion-shaped projections (14). It is thus possible to provide a medical guide wire that is inexpensive to manufacture and whose strength is unaffected and frictional resistance is low, and manufacturing method for the same.

10 Claims, 8 Drawing Sheets

U.S. PATENT DOCUMENTS

2002/0172829 A1    11/2002   Mori et al.

FOREIGN PATENT DOCUMENTS

| | | |
|---|---|---|
| EP | 0 964 037 A1 | 12/1999 |
| JP | 56-63365 | 5/1981 |
| JP | 3-41966 | 2/1991 |
| JP | 11-19217 | 1/1999 |
| JP | 11-504829 | 5/1999 |
| JP | 11-178930 | 7/1999 |
| JP | 2000-509641 | 8/2000 |
| JP | 2000-271132 | 10/2000 |
| JP | 2001-238962 | 9/2001 |
| JP | 2002-95735 | 4/2002 |
| WO | WO98/38258 | 9/1998 |

* cited by examiner

MEDICAL GUIDE WIRE AND PROCESS FOR PRODUCTION THEREOF

TECHNICAL FIELD

The present invention relates to medical guide wires used in guiding a catheter directly, or inserted through a blood vessel, into a person's body during a test or a medical procedure, and methods for manufacturing the same.

BACKGROUND ART

Medical acts performed on the body impose a significant burden on the patient, and thus testing and medical procedures on the body have come to be performed by inserting a medical device such as a catheter directly into a body cavity in place of the conventional approach of making an incision. When using a catheter in this manner, a guide wire is passed through a catheter that is to be introduced to a target site within the body, and then the catheter is guided along the guide wire to that target site.

When inserting a catheter, the guide wire serving as the guide is inserted first and then the catheter is inserted into the body along the guide wire, and when there is little clearance between the catheter and the guide wire, or due to the blood influx at the time of insertion into the body, frictional resistance occurs and causes the guide wire to come into intimate contact with the inner circumferential surface of the catheter, increasing the likelihood of trouble. Consequently, to lower the frictional resistance between the guide wire and the catheter, the guide wire, that is, the core wire, is coated with fluororesin so that the guide wire can pass through the catheter with ease (JP H3-41966A).

However, although a guide wire whose core wire surface has been evenly coated with a fluororesin exhibits lower frictional resistance due to the low friction properties afforded by the fluororesin, the fluororesin comes into intimate contact with the inner circumferential surface of the catheter because it is applied evenly, and thus its effect was not sufficient. Accordingly, other proposals have been forwarded to further reduce the frictional resistance between the catheter and the guide wire, including providing the outer circumferential surface of the guide wire itself with an uneven shape having recessions and protrusions (JP H11-19217A), and wrapping a helical coil around its outside (JP H11-178930A, Tokuhyo 2000-509641).

However, in each of these conventional examples it was necessary to process the core material, and this complicated manufacturing, and there were also problems such as a change in the properties of the wire, for example its strength and modulus of elasticity, due to processing the core material, and an increase in costs due to core material processing, and moreover, there was the problem that the frictional resistance was not significantly improved.

DISCLOSURE OF INVENTION

In order to solve the foregoing conventional problems, it is an object of the present invention to provide a medical guide wire that is inexpensive to manufacture and whose strength is unaffected and frictional resistance is low, and a manufacturing method for the same.

A medical guide wire of the present invention is a medical guide wire in which at least a fluororesin coating layer is formed on a surface of a metal wire, wherein particulate matter is present in the fluororesin coating layer, and the fluororesin coating layer covers the particulate matter and at least some of the particulate matter is formed in surface protrusion-shaped projections.

A method for manufacturing a medical guide wire of the present invention is a method for manufacturing a guide wire, in which at least a fluororesin coating layer is formed on a surface of a metal wire, that includes mixing particulate matter for projections into a fluororesin dispersion to prepare a coating solution, applying the solution to the surface of the metal wire and drying the solution, and then baking by heating to at least the melting point of the fluororesin in the fluororesin dispersion, to cause particulate matter to be present in the fluororesin coating layer, wherein the fluororesin coating layer covers the particulate matter and at least some of the particulate matter is formed in surface protrusion-shaped projections.

Another method for manufacturing a medical guide wire according to the present invention is a method for manufacturing a medical guide wire, in which a primer layer and a fluororesin coating layer are formed in that order on a surface of a metal wire, that includes mixing particulate matter into at least one solution selected from a primer solution and a fluororesin dispersion solution, applying the primer solution and the fluororesin solution to the surface of the metal wire in that order and drying them, and then, in a final process, baking by heating to at least the melting point of the fluororesin in the fluororesin dispersion such that the fluororesin coating layer of the outermost layer covers the particulate matter and at least some of the particulate matter is formed in surface protrusion-shaped projections.

Figure 1:
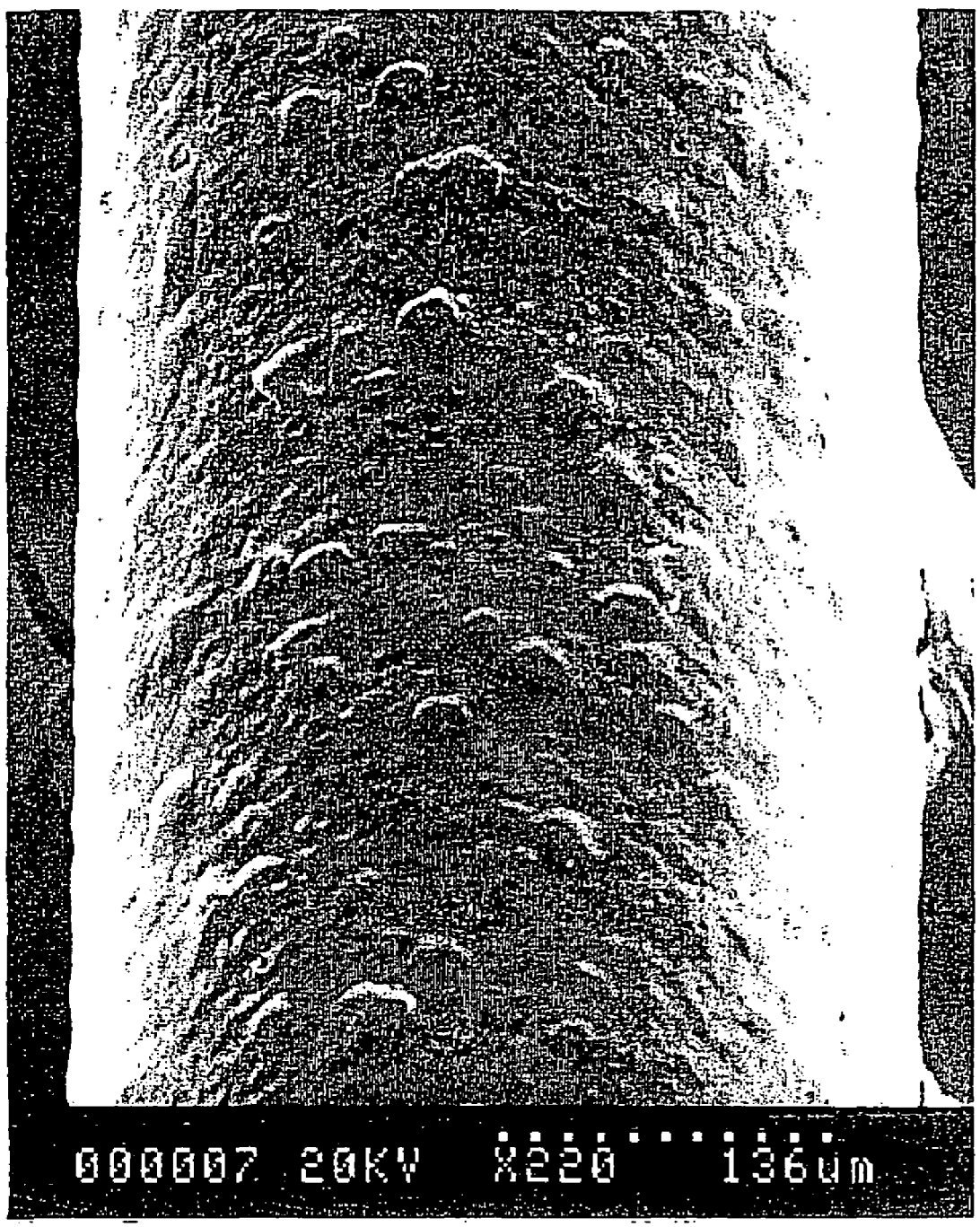
FIG. 1 is a SEM photograph (220×) external view of the fluororesin coated wire obtained in Working Example 1 of the present invention.

1,20 fluororesin coated wire
2 tube made of resin
3 metal jig
4 clip
5 tensile tester
7 fastened chuck
11,21 superelastic alloy wire
12,22 primer layer
13,23 fluororesin coating layer
14,24 projections
25 aluminum borate particles

BEST MODE FOR CARRYING OUT THE INVENTION

In the present invention it is possible to provide the particulate matter in either or both the primer layer and the fluororesin coating layer. In a final process, by baking by heating to at least the melting point of the fluororesin in the fluororesin dispersion, the fluororesin coating layer of the outermost layer covers the particulate matter. Particulate matter having a predetermined average particle diameter is used, and of these, comparatively large particles and agglomerated particles are formed in surface protrusion-shaped projections.

In a preferable example of the present invention, the fluororesin coating layer and the protruding projection-like fluororesin portions are baked as a single unit. Thus, the projection-like fluororesin particles are formed in smooth projections, and this contributes to lowering the frictional resistance. In other words, if the projections are smooth, then an object (resin tube) that comes into contact with them makes point contact, lowering the frictional resistance. As a result, this is useful for the medical guide wire for catheters, for example.

In the foregoing, whether or not the projections are smooth is determined based on observations made at 200× magnification by scanning election microscope (SEM). When the magnification ratio is too small (for example, observations by the unaided eye), many of the projections will appear relatively smooth, whereas when the magnification ratio is too high (for example, 1000×), then many of the projections will appear extremely steep. Consequently, choosing the magnification ratio is very important. It should be noted that at a magnification ratio of 200×, the diameter portion of a medical guide wire whose diameter is approximately 0.35 mm fits into a single field of view, allowing the entire diameter portion to be observed and thus is favorable.

If the fluororesin coating layer includes particulate matter, then it is preferable that the particulate matter is fluororesin. The two being compatible allows them to be baked into a more robust single unit.

It is preferable that the fluororesin coating layer and the fluororesin projections include at least one selected from polytetrafluoroethylene (PTFE), tetrafluoroethylene-perfluoroalkylvinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE). Of these, at least one selected from polytetrafluoroethylene (PTFE) and tetrafluoroethylene-perfluoroalkylvinyl ether copolymer (PFA) is preferable. This is because of their relatively high melting point and the fact that they are safe for the human body.

It is preferable that the thickness of the fluororesin coating layer is at least 1 μm and not more than 50 μm. This is because this thickness does not effect the medical operation of the wire. It is also preferable that the average height of the projections is at least 0.1 μm and not more than 20 μm. This range is ideal for lowering friction. It is also preferable that the fluororesin coating layer surface has a mixture of flat portions and numerous projections. This shape is ideal for improving the friction characteristics. It is further preferable that the density of the protrusion-shaped fluororesin portions is at least an average of 1 per 0.01 $mm^2$ in order to lower friction.

Also, whereas it is preferable to have projection-like protrusion shapes in the fluororesin coating layer surface, to improve the roundedness of these projections, it is preferable that a fluororesin is coated onto a wire surface and baked to achieve a fluororesin coating layer by melting to form flat portions and also baking to melt the fluororesin particles for projections in a single unit with the fluororesin coating layer and form projection portions that after baking take on a smooth particle shape, thereby contributing to their roundness. To this end, it is preferable that non-baked fluororesin particles are dispersed in liquid to form the fluororesin dispersion, and also that particles that have been baked are mixed in with the fluororesin particles for projections.

It is also preferable to mix fluororesin having different melting points, and by mixing fluororesin particles having a higher melting point than the fluororesin dispersion into the fluororesin dispersion, which has a lower melting point, it is possible to form a fluororesin coating layer with excellent roundedness in which deformation of the fluororesin particles due to melting is suppressed. For example, it is possible to mix PTFE (melting point 327° C.) particles for projections into a dispersion of FEP (melting point 255 to 265° C.) or PFA (melting point 305° C.), or to mix PTFE particles for projections that have been baked into a non-baked PTFE dispersion, and depending on the conditions, various combinations of these are possible.

A method for manufacturing a medical guide wire of the present invention is a method for manufacturing a guide wire, in which a fluororesin layer is formed on a surface of a metal wire, that includes mixing fluororesin particles for projections into a fluororesin dispersion to prepare a coating solution, applying the solution to the surface of the metal wire, and then baking by heating to at least the melting point of the fluororesin dispersion, thereby forming a fluororesin coating and projection-like fluororesin portions protruding from the fluororesin coating as a single unit on the surface of the metal wire, forming rounded projections.

The method for applying the fluororesin dispersion or the primer solution to the guide wire surface can be any one of brushing, spraying, or the like, but in order to achieve a uniform application, a dipping method is preferable. The temperature at which the fluororesin is baked is between 300 and 450° C., and thus after baking the fluororesin coated wire, the fluororesin is cooled quickly from a molten state, thereby annealing the metal wire and preventing the loss of rigidity as well as obtaining a hard coating layer due to the fluororesin layer cooling quickly. Here, cooling quickly means cooling of the fluororesin from a molten state at a rate of about 50 to 100° C. per second. The preferable conditions can be determined based on the wire diameter and material of the metal wire and the thickness and baking temperature of the fluororesin.

In the method of the invention, it is preferable that the fluororesin solid content concentration in the fluororesin dispersion for coating is 20 to 60 wt %. Within this range, the dispersion is stable.

It is preferable that when A is an amount of the fluororesin particles for forming projections that is added and B is the solid content of the fluororesin dispersion, then $[A/(A+B)] \times 100$ is 1 to 60 wt %. This is because it gives favorable low friction properties. It is preferable that the average particle diameter of the fluororesin microparticles for coating within the fluororesin dispersion is approximately 0.20 to 0.30 μm when measured by a light dispersion method. It is also preferable that the average particle diameter of the fluororesin particles for projections is at least 0.5 and not more than 30 μm. This range is ideal for lowering friction. It should be noted that if the diameter of the fluororesin particles for projections is larger than the thickness of the fluororesin coating, then because they are baked into a single unit with the fluororesin for coating, most are deformed due to melting and become smooth projections. If the diameter of the fluororesin particles for projections is smaller than the thickness of the fluororesin coating, then the amount of fluororesin particles for projections that is added can be increased to stack the particles on one another and thereby cause them to protrude from the coating.

In the present invention it is possible to mix particulate matter into the primer layer. By doing this, the fluororesin coating layer, which is the outermost layer, covers the particulate matter, allowing the particulate matter to form protrusion-shaped surface projections. Here, the primer layer is a layer for increasing the intimacy of contact between the metal surface of the guide wire and the outermost fluororesin layer. In this case, it is preferable that the particulate matter is fluororesin or a heat-resistant substance having a higher melting point than the fluororesin coating layer. This is because projections of particle are formed conspicuously after the fluororesin is baked. The particulate matter can be at least one type of particle selected from fluororesin, glass, metal, plastic, inorganic powder, and ceramic. It is preferable that the average particle diameter of the particulate matter is at least the film thickness of the primer layer, and preferably the average particle diameter is in the range of 0.5 to 30 μm. It is also preferable that the thickness of the fluororesin coating layer is at least 1 μm and not more than 50 μm. It is also preferable that the average height of the projections is at least 0.1 μm and not more than 20 μm. It is also preferable that the amount of particulate matter that is present is 1 to 50 wt % with respect to the solid content mass of the primer solution.

A metal wire that has a uniform thickness or whose tip is tapered can be employed favorably as the metal wire in the present invention. The wire material is preferably a superelastic alloy, and for example is Ti—Ni (Ni: 49-51 atomic %, including Ti—Ni to which a third element has been added), Cu—Al—Zn (Al: 3-8 atomic %, Zn: 15-28 atomic %), Fe—Mn—Si (Mn: 30 atomic %, Si: 5 atomic %), Cu—Al—Ni (Ni: 3-5 atomic %, Al: 28-29 atomic %), Ni—Al (Al: 36-38 atomic %), Mn—Cu (Cu: 5-35 atomic %), or Au—Cd (Cd: 46-50 atomic %). These alloys are known as superelastic alloys or shape memory alloys. Of these, a Ti—Ni alloy is preferable. Its thickness preferably is selected based on the inner diameter of the catheter with which it is to be used in combination. More specifically, wires having a diameter of approximately 0.3 mm to 1 mm are frequently used.

WORKING EXAMPLES

Hereinafter, the present invention is described in more specific detail using working examples.

(1) Method of Measuring the Frictional Resistance

Figure 3:
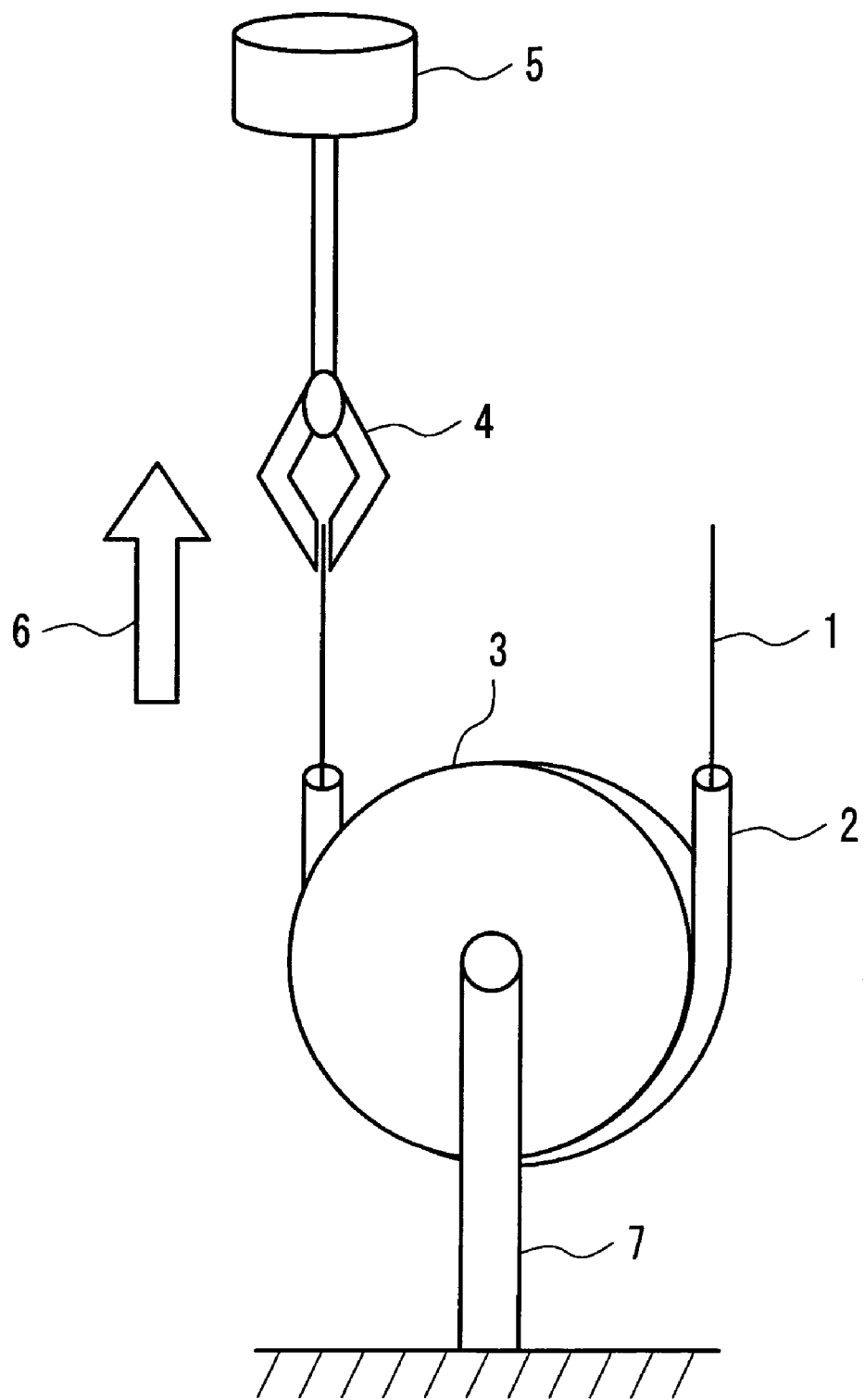
FIG. 3 is an explanatory diagram showing the method for measuring the frictional resistance in the working examples of the present invention.

As shown in FIG. 3, a polyurethane resin tube (inner diameter 2.5 mm, outer diameter 4.0 mm, length 200 mm) 2 is fixedly adhered over half its circumference to a metal jig 3 having a diameter of 90 mm, and the jig 3 is attached to a fastened chuck 7 of a tensile tester.

Next, a fluororesin coated wire 1 is inserted into the polyurethane resin tube and one end of the wire is fastened to a clip 4 of the tensile tester 5, while the other free end is pulled at a velocity of 50 mm per minute in the direction of an arrow 6, and by measuring the load at this time, the frictional resistance between the wire 1 and the polyurethane resin tube was measured. The smaller the tensile strength, the smaller the frictional resistance. The measurement was performed by measuring the frictional resistance over any 50 mm portion of the guide wire, and recording those values to a chart and calculating an average value from the data.

(2) Method of Measuring the Height of the Projections Coated by Fluororesin

Measurement was performed under the following conditions using the super depth-shape measuring microscope "VK-8550" made by KEYENCE CORPORATION of Japan.
Emission Laser: semiconductor laser, wavelength 685 nm
Output: 0.45 mW
Magnification Ratio: 100×
Measurement Depth: 5 μm
Movement Pitch: 0.05 μm
Laser Scan: 9 Hz
Laser Emission Angle: Vertical (emission straight downward from above, and reflection light is received by a light-receiving portion)

Figure 8:
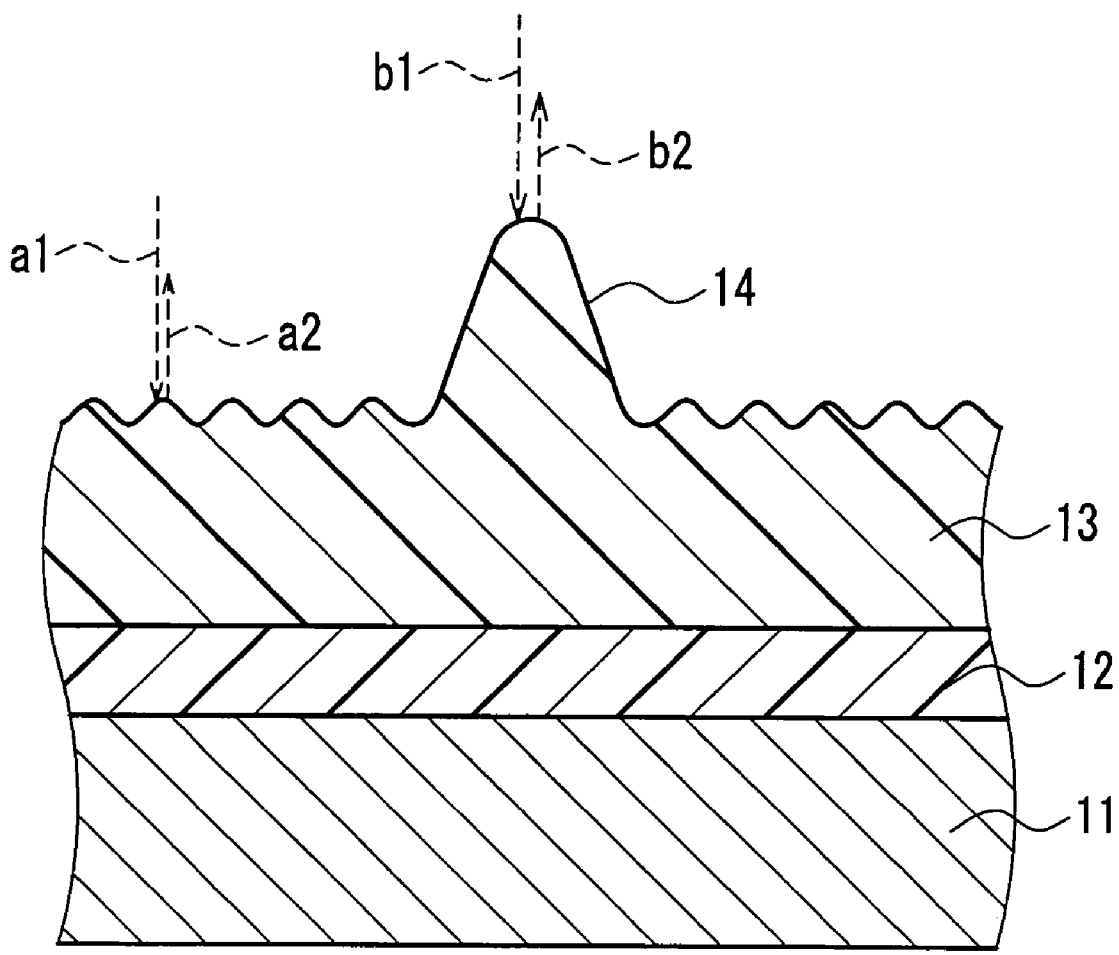
FIG. 8 is an explanatory diagram showing the method for measuring the height of the projections in the working examples of the present invention.

Regarding the measuring method, as shown in FIG. 8 a laser light a1 is emitted straight down and the reflection light a2 is received by a light-receiving portion that is not shown, and from its focal length the distance (depth) of the section in question is measured. Projections 14 also are measured in this fashion, emitting a laser light b1 and receiving reflection light b2, and from that focal length obtaining the distance of that position by measurement. In other words, the unevenness of a sample is successively obtained by measurement over a fixed area of the sample from that focal length, calculating the height of the projections 14 regarding the a1 emission portions as flat portions. Measurements are calculated as the average value of five measured values per sample.

Working Example 1

A primer solution ("855-300" made by Dupont) having a 35% solid portion concentration) adjusted to a viscosity of 110 cp (23° C.) was coated onto a 2 m length, 0.35 mm diameter Ti—Ni (Ni: 49-51 atomic %) superelastic alloy wire to a dried thickness of approximately 1 μm and then dried naturally at room temperature for 10 minutes. It was then heated at 150° C. for 30 minutes.

Separately, a fluororesin dispersion for coating ("855-510" made by Dupont) was used as the fluororesin of the outermost layer. The fluororesin solid concentration was 50 wt %. PTFE particles for forming projections ("L150J" made by Asahi Glass) (average particle diameter approximately 9 μm) were added to this dispersion to 20 wt % with respect to the fluororesin mass of the dispersion and then mixed, and this was taken as the coating liquid.

The coating liquid was coated over the wire, which had been coated by the primer solution, dried naturally at room temperature (25° C.) for 1 minute, heated at 200° C. for 10 minutes, then baked at 450° C. for 1 minute and cooled to room temperature. The thickness of flat portions of the fluororesin coating layer was approximately 5 μm, and the average height of projections was approximately 3.5 μm.

FIG. 1 shows the external appearance of the fluororesin coated wire obtained in this manner. FIG. 1 is a scanning electron microscope (SEM) photograph taken at 200× magnification. It is clear from FIG. 1 that a fluororesin coating layer and projections at a ratio of at least an average of 1 per 0.01 $mm^2$ are formed in the fluororesin coating layer surface, that the fluororesin particles and the fluororesin are baked into a single unit, and that the projection-like fluororesin particles are formed in smooth protrusions.

Figure 2:
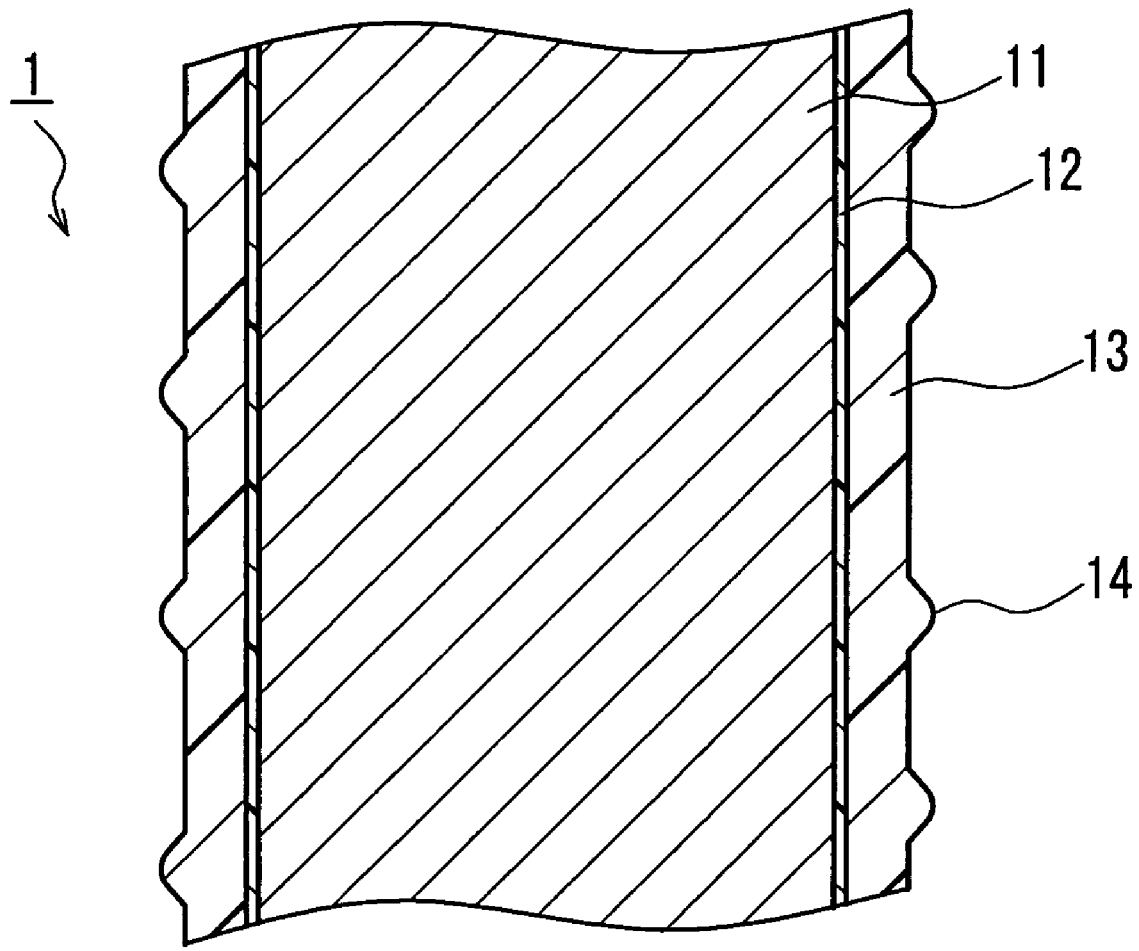
FIG. 2 is a schematic cross-sectional view of the same.

FIG. 2 is a schematic cross-sectional view of FIG. 1. The fluororesin coated wire 1 is made of a primer layer 12, a fluororesin coating layer 13, and projections 14 due to the fluororesin particles, baked into a single unit on the surface of a superelastic alloy wire 11.

The frictional resistance of the fluororesin coated wire thus obtained was measured. The result was an average frictional resistance value for the wire of Working Example 1 of 2.0 g.

Working Example 2

Other than using a dispersion in which microparticles of PFA, which have a lower melting point than PTFE, have been dispersed for the fluororesin coating dispersion for the coating of Working Example 1 and changing the baking temperature when baking to form the fluororesin coating, the same experiment as that of Working Example 1 was performed. PTFE particles for forming projections (average particle diameter approximately 9 μm) were added to the dispersion of PFA microparticles to 20 wt % with respect to the fluororesin mass and mixed and then coated onto a 2 m length, 0.35 mm diameter superelastic alloy wire. After coating was finished, the result was dried naturally at room temperature for 1 minute, heated at 200° C. for 10 minutes, then baked at 380° C. for 1 minute and cooled to room temperature. The thickness of the flat portions of the fluororesin coating was approximately 5 μm, and the average height of the projections was approximately 4 μm. The average frictional resistance value of the wire of Working Example 2 was 1.8 g.

Comparative Example 1

Other than no PTFE particles for forming projections being added to the fluororesin dispersion in Working Example 1, the same fluororesin coating as in Working Example 1 was formed.

Figure 4:
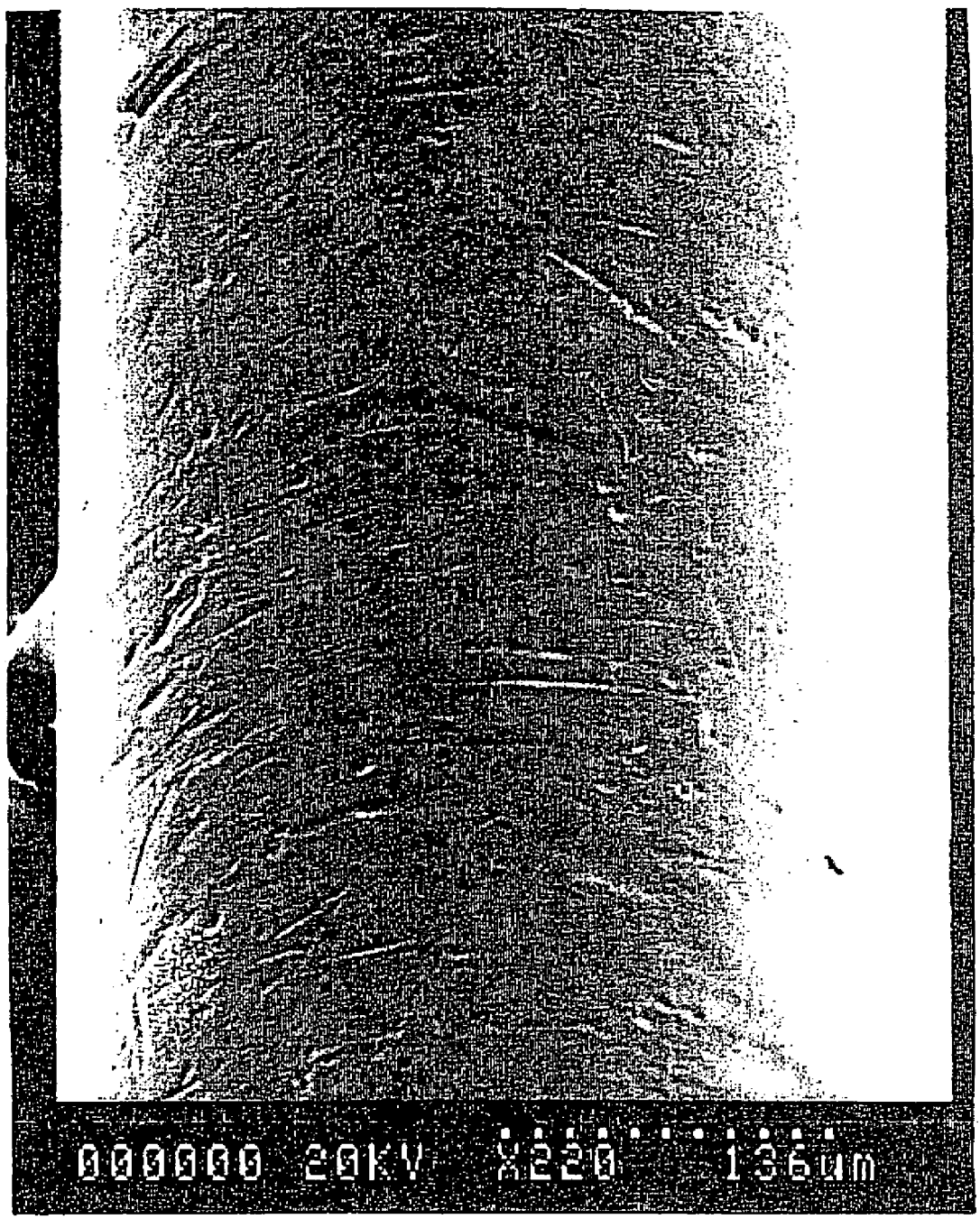
FIG. 4 is a SEM photograph (220×) external view of the fluororesin coated wire obtained in Comparative Example 1 of the present invention.

FIG. 4 shows the external appearance of the fluororesin coated wire. FIG. 4 is a scanning electron microscope (SEM) photograph taken at 200× magnification. It is clear from FIG. 4 that a fluororesin coating layer having a uniform thickness was formed.

The frictional resistance value of this fluororesin coated wire was measured in the same manner as in Working Example 1, and the average frictional resistance value of the wire was found to be 4.5 g.

Comparative Example 2

PTFE particles having an average particle diameter of 9 μm were applied as a fine powder over the wire surface and the fluororesin was baked for 1 minute at a temperature of 450° C.

Figure 5:
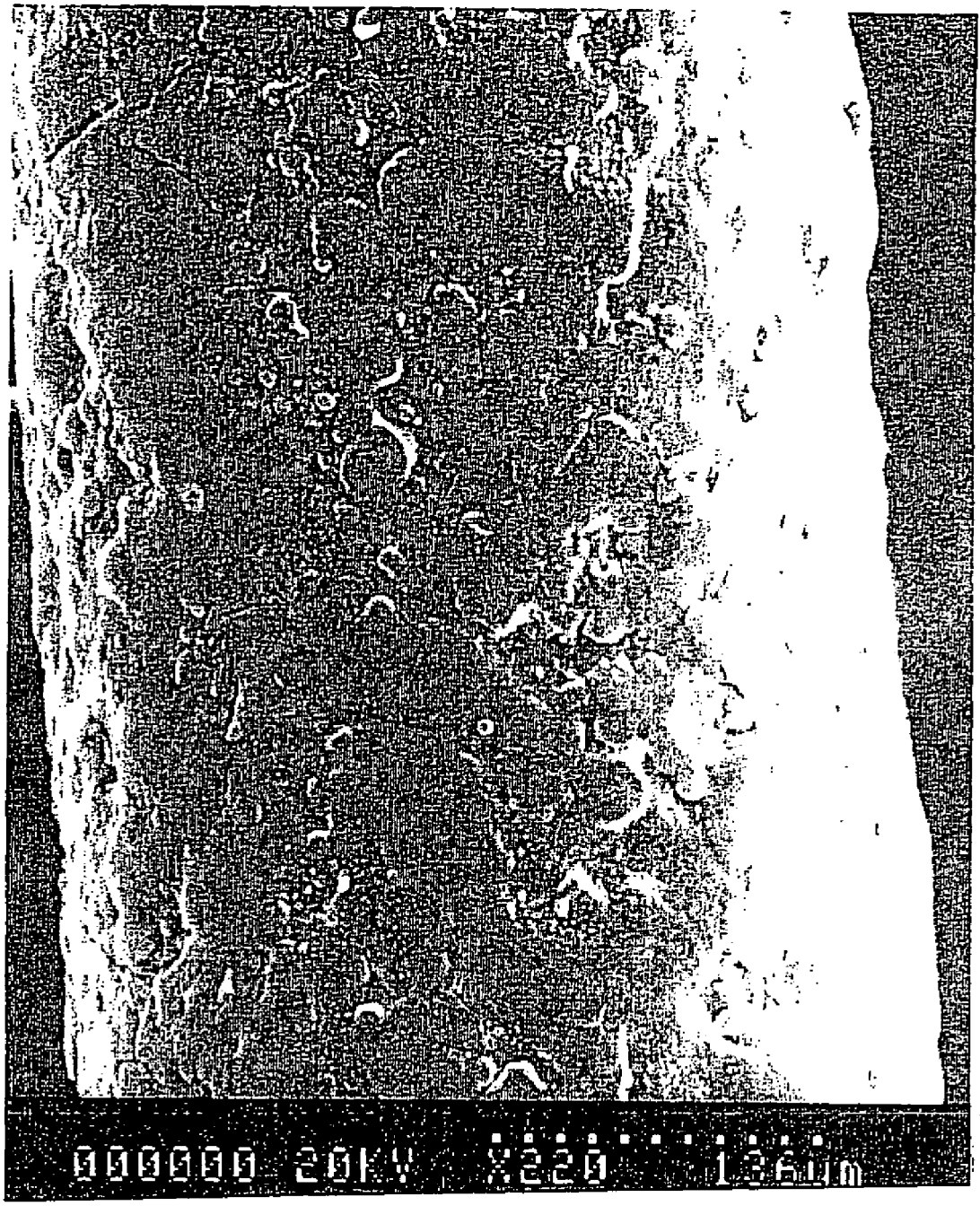
FIG. 5 is a SEM photograph (220×) external view of the fluororesin coated wire obtained in Comparative Example 2 of the present invention.

FIG. 5 shows the external appearance of the fluororesin coated wire. FIG. 5 is a scanning electron microscope (SEM) photograph taken at 200× magnification. It is clear from FIG. 5 that the fluororesin coating layer has an uneven shape.

The frictional resistance of this fluororesin coated wire was measured as in Working Example 1, and the average frictional resistance value of the wire was found to be 3.8 g.

Working Example 3

A 2 m length, 0.35 mm diameter Ti—Ni (Ni: 49-51 atomic %) superelastic alloy wire was prepared. Next, 10 wt % aluminum borate "PF03" (made by Shikoku Chemicals Corporation) having a 3 μm average particle diameter was mixed in and dispersed to "855-300" (made by Dupont) having a 35% solid concentration to serve as a primer solution, and its viscosity was adjusted to 110 cp (23° C.). The primer was then coated by an immersion method until a dried thickness of approximately 1.0 μm, dried naturally at room temperature for 10 minutes, and then heated at 150° C. for 30 minutes. Regarding the dried primer coating surface, the numerous aluminum borate projections precipitated on the wire surface were applied along with the primer coating.

Next, a fluororesin dispersion for coating ("AD-1" made by Asahi Glass), where the average diameter of the fluororesin microparticles made of PTFE was measured by light dispersion to be approximately 0.20 μm, was used for the outermost fluororesin layer. The fluororesin solid content concentration was 60 wt %, and using (Triton) polyoxyethylene (10) octylphenyl ethyl was adjusted to a viscosity of 150 CP, and this dispersion was taken as the coating liquid of the outermost fluororesin layer.

This coating liquid was coated by dripping onto the surface of the wire that had been coated with the primer solution, dried naturally at room temperature for 1 minute, heated at 200° C. for 10 minutes, then baked at 400° C. for 1 minute and cooled to room temperature. The thickness of the flat portions of the fluororesin coating layer was approximately 6 μm, and the average height of the projections was approximately 2.0 μm.

Figure 6:
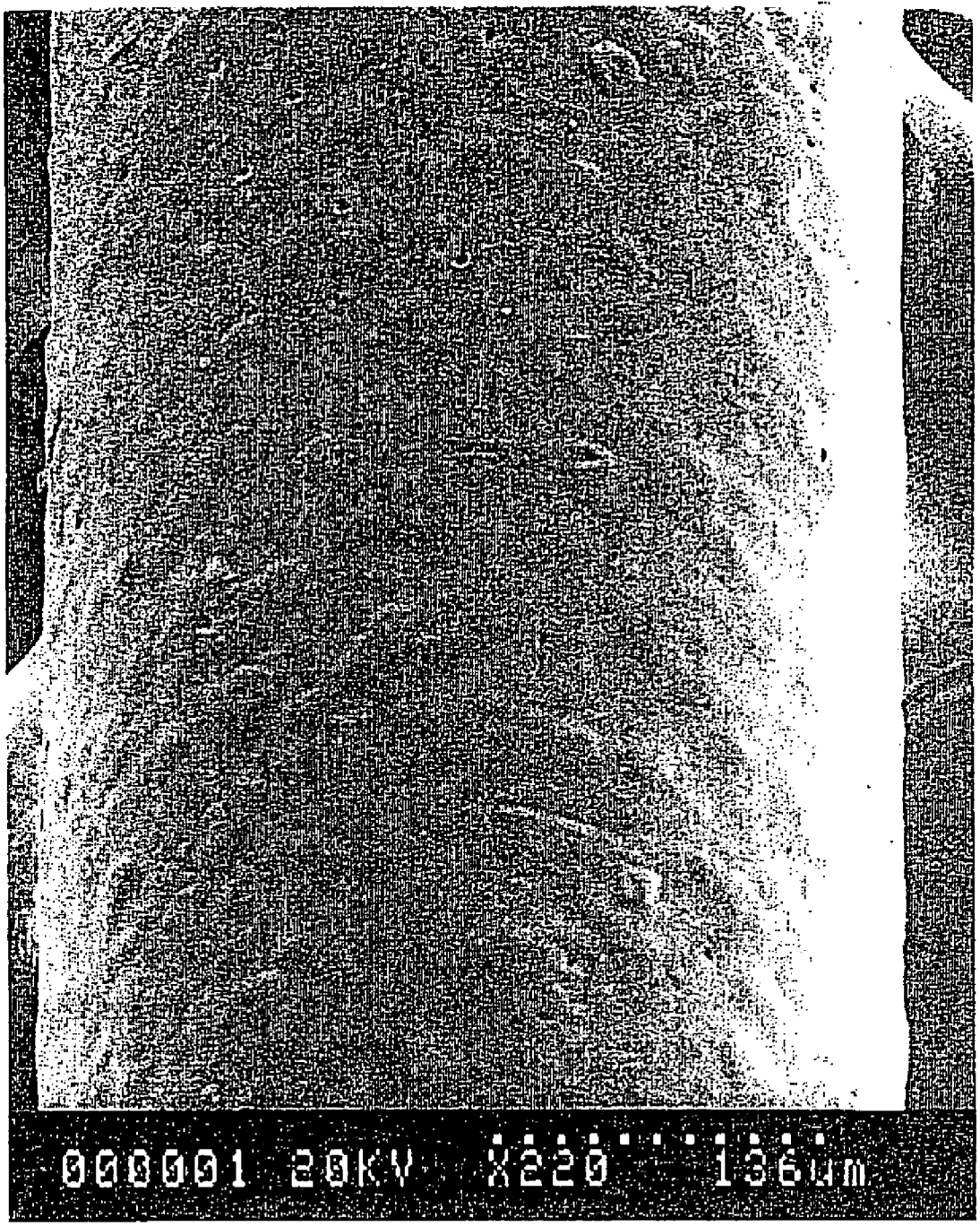
FIG. 6 is a SEM photograph (220×) external view of the fluororesin coated wire obtained in Working Example 3 of the present invention.

FIG. 6 shows the external appearance of the fluororesin coated wire obtained in this manner. FIG. 6 is a scanning electron microscope (SEM) photograph taken at 200× magnification. It is clear from FIG. 6 that a guide wire having a coating layer in which the projection-like shapes of the aluminum borate particles mixed into the primer solution were formed as rounded projections coated by the fluororesin on the fluororesin coating layer surface was obtained.

Figure 7:
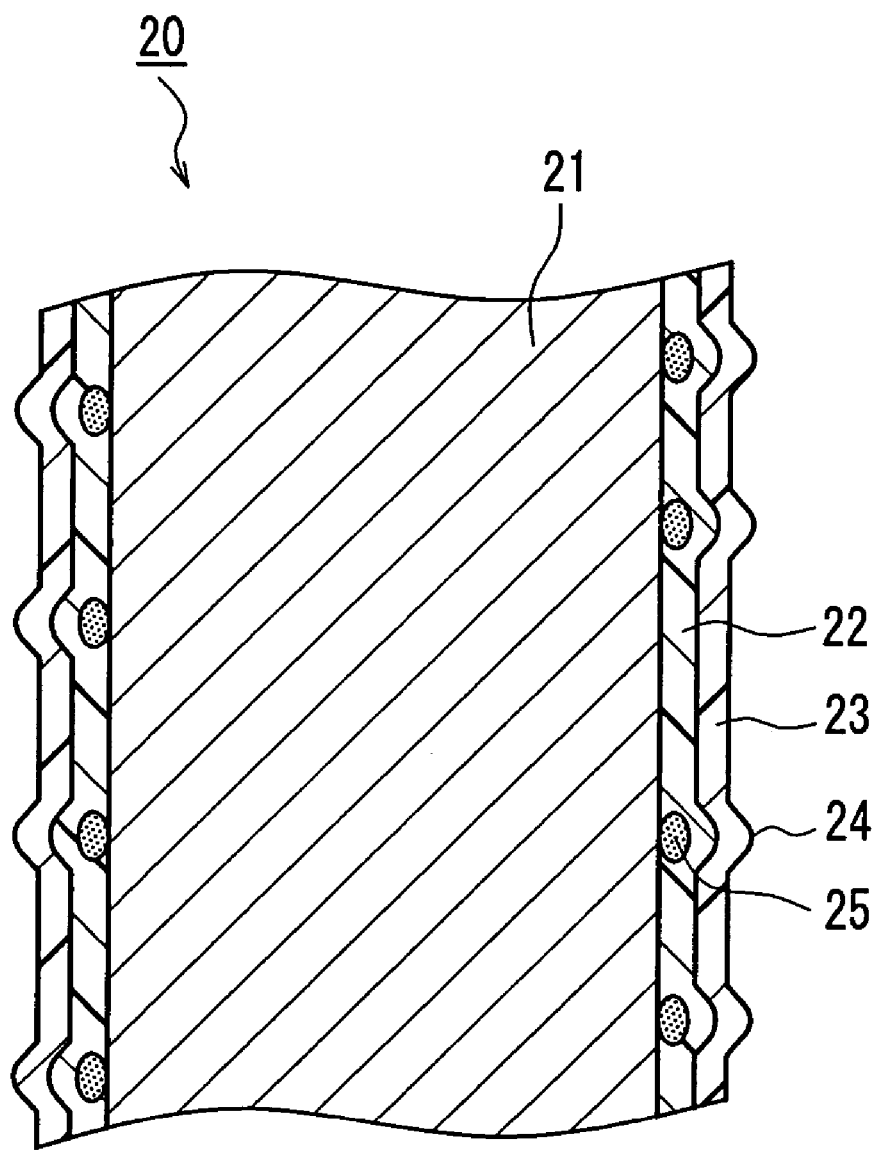
FIG. 7 is a schematic cross-sectional view of the same.

FIG. 7 is a schematic cross-sectional view of the guide wire of this working example. A fluororesin coated wire 20 is made of a primer layer 22, to which aluminum borate particles 25 have been mixed, and a fluororesin coating layer 23 layered onto the surface of a superelastic alloy wire 21, and the projections 24 in which the aluminum borate particles 25 are coated by the fluororesin layer are coated such that they form smooth projection shapes.

The average frictional resistance value of the fluororesin coated wire thus obtained was 1.5 g.

Working Example 4

To the primer solution of Working Example 3, PTFE particles ("L150J" made by Asahi Glass) (9 μm average particle diameter) were added in place of the aluminum borate to 20 wt % with respect to the solid concentration of the primer solution and this was mixed, and then this primer solution was coated by immersion to a thickness of 2 μm onto a 2 m length, 0.35 mm diameter superelastic alloy wire. The primer solution was then dried naturally at room temperature for 10 minutes and heated at 150° C. for 30 minutes and dried. Regarding the dried primer coated surface, the numerous fluororesin projections precipitated on the wire surface were applied along with the primer coating. Then, coating by immersion using a dispersion in which microparticles of PFA, which have a lower melting point than PTFE, are dispersed was performed, this was dried naturally at room temperature for 1 minute, heated at 200° C. for 10 minutes, then baked at 380° C. for 1 minute and cooled to room temperature. The thickness of the flat portions of the fluororesin coating was approximately 7 μm, and the height of the projections was approximately 5 μm. The average frictional resistance value was 1.8 g.

It is clear from the above working examples and comparative examples that the wire of the present invention, in which a fluororesin coating layer and fluororesin particles for forming projections are baked as a single unit and the projection-like fluororesin particles form smooth protrusions, had the lowest frictional resistance value.

INDUSTRIAL APPLICABILITY

With the medical guide wire of the present invention, the fluororesin coating layer and the projections made of particulate matter protruding from the fluororesin coating layer surface are baked into a single unit and the protrusions are formed rounded, and thus the frictional resistance between the catheter and the guide wire can be reduced, making the action of inserting the catheter into the body easy. Also, it is not necessary to process, for example deform, the core material itself, and thus characteristics of the core material such as its strength and modulus of elasticity can be utilized as they are.

With the method of the present invention it is possible to effectively, efficiently, and inexpensively manufacture the medical guide wire of the present invention.

The invention claimed is:

1. A fluororesin coated medical guide wire, comprising:
a metal wire;
a primer layer covering at least a portion of a surface of the metal wire; and
a fluororesin coating layer formed further on an outside of the primer layer,
the fluororesin coating layer including a base layer made of a first fluororesin material, and surface protrusion-shaped smooth projections of a second fluororesin material,
wherein the surface protrusion-shaped smooth projections are particulate projections based on presence of the second fluororesin material, the first and the second fluororesin materials are compatibly melted together, the fluororesin coating layer having no clearly distinguishable boundary between the first fluororesin material and the second fluororesin material.

2. The medical guide wire according to claim 1,
wherein the second fluororesin material is also present in the primer layer; and
wherein an outermost layer of the fluororesin coating layer covers the second fluororesin material.

3. The medical guide wire according to claim 2, wherein an average particle diameter of the second fluororesin material is at least the film thickness of the primer layer, and the average particle diameter is in a range of 0.5 to 30 μm.

4. The medical guide wire according to claim 1, wherein the first and second fluororesin materials of the fluororesin coating layer include at least one selected from the group consisting of polytetrafluoroethylene (PTFE), tetrafluoroethylene-perfluoroalkylvinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE).

5. The medical guide wire according to claim 1, wherein the thickness of the fluororesin coating layer is at least 1 μm and not more than 50 μm.

6. The medical guide wire according to claim 1, wherein the average height of the projections is at least 0.1 μm and not more than 20 μm.

7. The medical guide wire according to claim 1, wherein the fluororesin coating layer surface has a mixture of flat portions and numerous protrusion-shaped projections.

8. The medical guide wire according to claim 1, wherein the density of the protrusion-shaped projections is at least an average of 1 per 0.01 $mm^2$.

9. The medical guide wire according to claim 1, wherein the first and the second fluororesin materials form a structural single unit.

10. The medical guide wire according to claim 1, wherein the first and the second fluororesin materials have different melting points.

* * * * *